United States Patent [19]

Miyazaki et al.

[11] Patent Number: 5,289,260
[45] Date of Patent: Feb. 22, 1994

[54] PATTERN DEFECT DETECTION DEVICE AND A SPATIAL FREQUENCY FILTER USED THEREIN

[75] Inventors: Yoko Miyazaki; Toshimasa Tomoda; Hitoshi Tanaka; Nobuyuki Kosaka; Toyomi Ohshige, all of Hyogo, Japan

[73] Assignee: Mitsubishi Denki Kabushiki Kaisha, Tokyo, Japan

[21] Appl. No.: 787,929

[22] Filed: Nov. 6, 1991

[30] Foreign Application Priority Data

| Nov. 9, 1990 | [JP] | Japan | 2-305215 |
| Nov. 9, 1990 | [JP] | Japan | 2-305216 |
| May 24, 1991 | [JP] | Japan | 3-120248 |
| Jun. 26, 1991 | [JP] | Japan | 3-180470 |

[51] Int. Cl.⁵ ............................. G01B 9/02
[52] U.S. Cl. ..................... 356/354; 356/357; 356/237; 356/239; 356/347
[58] Field of Search ............ 356/354, 237, 357, 239, 356/347

[56] References Cited

U.S. PATENT DOCUMENTS

| 3,970,841 | 7/1976 | Green | 250/201 |
| 4,000,949 | 1/1977 | Watkins | 356/165 |
| 4,330,775 | 5/1982 | Iwamoto et al. | 340/146.3 |
| 4,806,774 | 2/1989 | Lin et al. | 250/550 |
| 4,929,081 | 5/1990 | Yamamoto et al. | 356/354 |
| 5,067,812 | 11/1991 | Sugimura et al. | 356/237 |

FOREIGN PATENT DOCUMENTS

| 2552903 | 11/1975 | Fed. Rep. of Germany. |
| 3422345 | 6/1984 | Fed. Rep. of Germany. |
| 63-205775 | 8/1988 | Japan. |

Primary Examiner—Samuel A. Turner
Assistant Examiner—LaCharles Keesee
Attorney, Agent, or Firm—Lowe, Price, LeBlanc & Becker

[57] ABSTRACT

A spatial frequency filter used in a pattern defect detection device, including a pattern which includes a black spot having a diameter expanded by a controlled amount in comparison with the diameter of a black spot on a photosensitive plate obtained by exposure by diffracted light from a pattern on a model specimen

8 Claims, 11 Drawing Sheets

FIG. 4C $\phi = 0°$ $\phi = \phi_1$

PATTERN DEFECT DETECTION DEVICE AND A SPATIAL FREQUENCY FILTER USED THEREIN

BACKGROUND OF THE INVENTION

1. Field of the Invention

The present invention relates to a pattern defect detection device for detecting defection and foreign matters in patterns of a regular arrangement such as in a patterned semiconductor integrated circuit, and more particularly, to improvement of a spatial frequency filter used in such a pattern defect detection device.

2. Description of the Background Art

Figure 1:
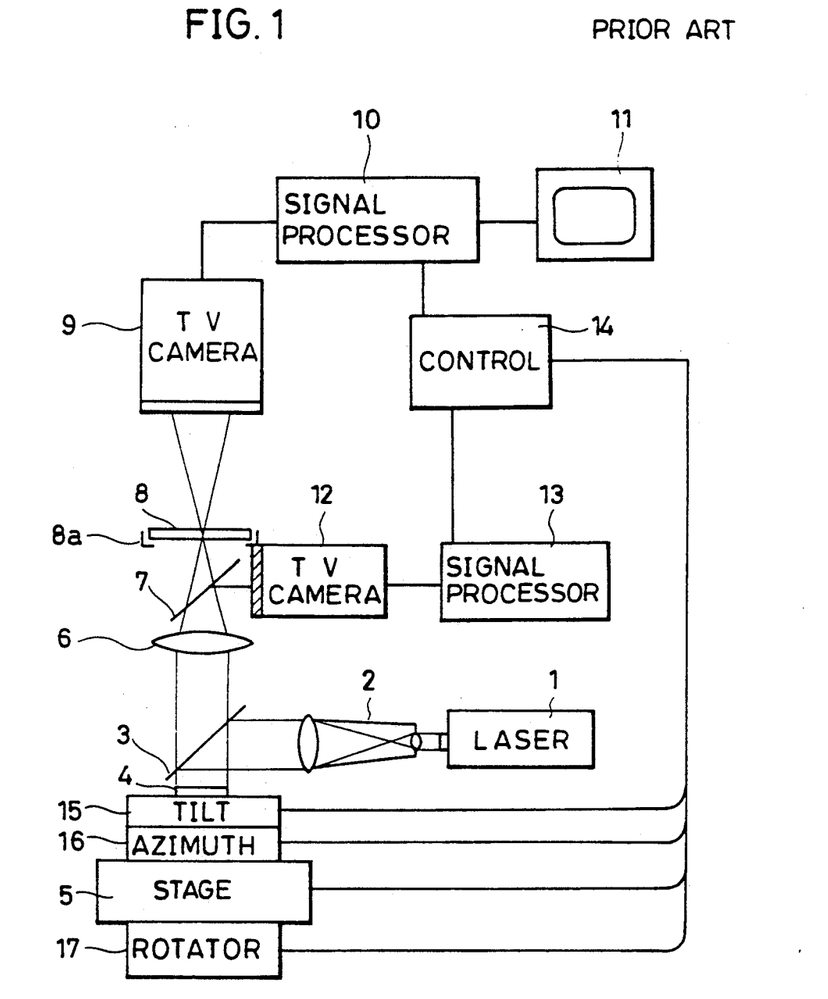
FIG. 1 is a block diagram showing a conventional pattern defect detection device.

FIG. 1 is a block diagram schematically showing a pattern defect detection device disclosed in Japanese Patent Laying-Open No. 63-205775. This pattern defect detection device includes a light source 1 of a laser oscillator and the like for generating coherent light, a collimator 2 to expand and collimate the coherent light emitted from source 1 to become parallel, a half mirror 3, a stage 5 for supporting a specimen 4 having a patterned surface, a lens 6 for focusing light diffracted by the pattern on the surface of specimen 4, a half mirror 7, and a spatial frequency filter 8 having a pattern of a plurality of black spots, supported in a holder 8a at the back focal plane of lens 6 for transmitting only diffracted light corresponding to the defection of the pattern and blocking diffracted light of a proper pattern.

The pattern defect detection device of FIG. 1 also includes a defect detection TV camera 9 (defection signal detection portion) for detecting diffracted light passing through the transparent portion of spatial frequency filter 8, i.e. through the portion other than the black spots, a first signal processor 10 for detecting the defect position according to the diffracted light detected by defect detection TV camera 9, a TV monitor 11 for displaying the defect, a position detection TV camera 12 for detecting the position of the diffraction pattern according to reflected light from half mirror 7, a second signal processor 13 for detecting the position of the diffraction pattern according to the reflected light detected by position detection TV camera 12, and a controller 14 to calculate the position offset distance from the proper position of the diffraction pattern according to the defect position and the diffraction pattern position detected by first and second signal processors 10 and 13 for sending a correction command to tilt-azimuth angle adjustment mechanisms 15, 16 and to a rotation angle adjustment mechanism 28.

The operation of the device of FIG. 1 will be explained hereinafter. The coherent light emitted from laser oscillator 1 is collimated into a parallel ray by collimator 2 and reflected by half mirror 3 to be directed to the pattern on specimen 4 such as a semiconductor integrated circuit wafer Diffracted light from specimen 4 passes half mirror 3 to be converged by lens 6 and divided into two by half mirror 7. The diffracted light passing half mirror 7 reaches to spatial frequency filter 8, whereas the diffracted light reflected by half mirror 7 enters position detection TV camera 12

At the time of defect detection, the diffracted light reaching to spatial frequency filter 8 through half mirror 7 has the component of proper pattern of specimen 4 removed by the pattern of black spots on spatial frequency filter 8, so that only the component of a defection is transmitted as a defection signal. This defection signal is received by defect detection TV camera 9 and detected by first signal processor 10. This defection is displayed on monitor 11.

During the defect detection, registration of the diffraction pattern represented by black spots on spatial frequency filter 8 and the pattern of the diffracted light of the proper pattern on specimen 4 must be carried out. More specifically, the diffracted light of half mirror 7 is observed by position detection TV camera 12, whereby the position of the diffracted light pattern is detected by second signal processor 13. The output signals of signal processors 10 and 13 are received by controller 14, whereby the position offset distance of the diffracted light pattern with respect to the position of the pattern of black spots on filter 8 is calculated from these output signals to provide an instruction to tilt-azimuth angle adjustment mechanisms 15, 16 and to rotation angle adjustment mechanism 17 to correct the deviation of the tilt-azimuth angle of the optical axis of the specimen 4 surface and the rotation angle Thus, a correct matching is carried out of the black spot pattern on spatial frequency filter 8 and the diffracted light pattern of proper pattern on specimen 4.

The above-described spatial frequency filter 8 is produced by exposing a photosensitive plate with a diffracted light pattern of a proper pattern at the back focal plane of lens 6. This filter 8 is then accurately positioned and fixed at the back focal plane of lens 6.

Since a conventional pattern defect detection device was implemented as described above, it was always necessary to accurately match the pattern of black spots on spatial frequency filter 8 and the diffracted light pattern by monitoring change in the angle of reflection of the wafer surface, i.e. the tilt-azimuth angle, to move stage 5 including tilt-azimuth angle adjustment mechanisms 15 and 16 during the defect detection.

The actual subject to be inspected, for example a semiconductor wafer, is subjected to various thermal treatments, wherein many have an undulating surface The undulating surface of specimen 4 attributed to a great correction of the tilt-azimuth angle, with a possibility that this correction may not be completed within a predetermined time period A great amount of correction required a long time period for this correction, leading to increase in the time required for the entire inspection. If defect detection was carried out when the correction of the tilt-azimuth angle was not thoroughly completed, there were some cases where the Fourier transform pattern of the black spot pattern on spatial frequency filter 8 and that of the pattern on specimen 4 do not match partially (or in some cases entirely). Light signal passing through the not-matching portion caused reduction in the ratio between the defection signal to be detected and the signal from the proper pattern which should not actually be detected, i.e. noise. This led to a problem that there was a limit in the minimum size of the defection that could be detected.

In specimen 4 having a complicated pattern such as in a semiconductor integrated circuit wafer where there is a pattern region including highly repetitive components such as memory cells, and a pattern region including few repetitive components that will reduce the diffracted light intensity to one order of magnitude lower, recording of the pattern region of the low repetition number could not be carried out sufficiently for creating a spatial frequency filter 8 just by a one time exposure on a photosensitive plate. A filter 8 not sufficiently recorded could not completely block the diffracted light pattern and passes weak remaining diffracted light pattern. On the contrary, if the photosensive plate is exposed until a spatial frequency filter 8 is obtained that has a spot of density that can completely block the diffracted light pattern from the pattern region of the low repetition number, the portion on the photosensive plate recording diffracted light from the pattern region of the high repetition number will have excessive exposure energy applied corresponding to the right end portion of the density curve of FIG. 2.

Figure 2:
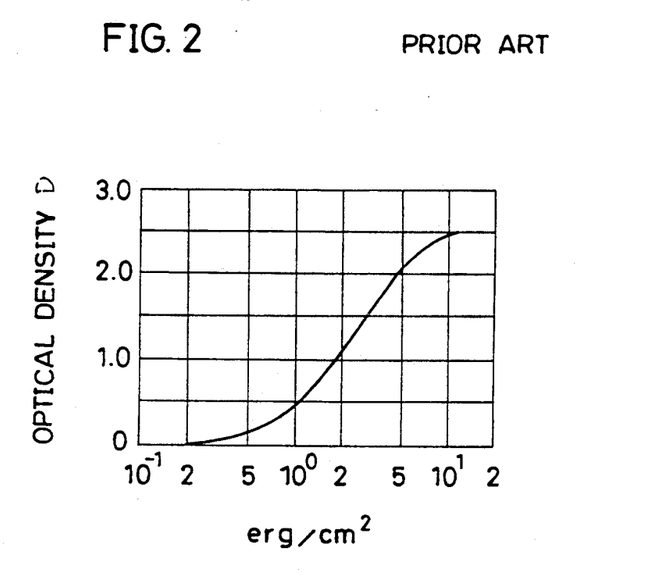
FIG. 2 is a graph showing an example of the photographic characteristic of a photosensitive plate.

Referring to the graph of FIG. 2, the abscissa shows exposure light energy (erg/cm$^2$) having a wave length of 633 nm, and the ordinate represents the optical density D of a photosensitive plate exposed by that light energy. The optical density D is defined as $D = \log_{10}(I_{in}/I_{out})$, where $I_{in}$ denotes intensity of incident light and $I_{out}$ denotes intensity of transmitted light. Overexposure occurs in the portion where diffracted light from the pattern region having many repetitive components are recorded to generate halation. This halation uncontrollably expands beyond the spot portion to be recorded to form unnecessary screening portions, whereby the defect signal transmittance of spatial frequency filter 8 is reduced. There is also a possibility of light being transmitted through a portion which should actually be a screening pattern portion. This means that detection will be carried out where remaining diffracted light pattern exists, leading to a problem that the region that can be detected correctly is limited to specific portions, such as in memory cells.

When spatial frequency filter 8 is formed by a photosensive plate such as a photosensitive material of silver halide emulsion, the density of the spots on filter 8 does not exceed a constant value, as shown in FIG. 2. More specifically, the light signal screening ability of spatial frequency filter 8 decreases the light intensity to only 1/1000-1/10000. This means that a proper pattern signal not blocked at the filter will pass therethrough to act as background noise, whereby the minimum size of the defection signal intensity that can be detected is inevitably determined. Therefore, a very small defection could not be detected that has a signal intensity that is less than 1/1000-1/10000 of the signal intensity from a proper pattern.

SUMMARY OF THE INVENTION

In view of the foregoing problems of conventional art, an object of the present invention is to provide a pattern defect detection device that can detect a weak defection signal in a short time by having a spatial frequency filter block effectively diffracted light from a normal pattern to minimize noise, without the need of correction of the tilt-azimuth angle of a specimen stage, even for specimens having an undulating surface and complex pattern such as in semiconductor integrated circuits.

Another object of the present invention is to provide a spatial frequency filter used in a pattern defect detection device eliminating the need of tilt-azimuth angle correction of a specimen stage.

A further object of the present invention is to provide a spatial frequency filter used in a pattern detect detection device that allows pattern defect detection of high sensitivity.

Yet another object of the present invention is to provide a spatial frequency filter that allows accurate pattern defect detection even when a pattern including many repetitive components and a pattern including few repetitive components exist in combination on a specimen.

A pattern defect detection device according to an aspect of the present invention includes a stage for supporting a specimen having a pattern on the surface thereof; a mirror for directing coherent light to the pattern on the specimen, wherein the mirror includes a mirror angle modify mechanism that changes the angle of reflection of coherent light; a lens for focusing light diffracted by the pattern on the specimen; a plate holder for holding one of a photosensitive plate to form a spatial frequency filter and a formed spatial frequency filter at the back focal plane of the specimen; and a defection signal detector for detecting light passing the spatial frequency filter as a detection signal corresponding to a defect in the pattern on the specimen.

A pattern defect detection device according to another aspect of the present invention is similar to that of the prior aspect, except that a moving mechanism that can move a photosensitive plate in two dimensional directions crossing the diffracted light is included instead of the mirror angle modify mechanism.

A spatial frequency filter used in a pattern defect detection device according to a further aspect of the present invention includes a pattern of a black spot having a diameter expanded by a controlled amount in comparison with the diameter of a black spot on a photosensitive plate obtained by exposure by diffracted light from a pattern not having defection on a model specimen.

A method of manufacturing a spatial frequency filter used in a pattern defect detection device according to still another aspect of the present invention includes the steps of: directing coherent light to a pattern not including defection on a model specimen; focusing diffracted light from the pattern not including defection onto a photosensitive plate by a lens, while changing the tilt-azimuth angle of the specimen so that the incident angle of coherent light varies within a predetermined range; and developing the exposed photosensitive plate.

A method of manufacturing a spatial frequency filter used in a pattern defect detection device according to a still further aspect of the present invention includes the steps of: directing coherent light from a light source to a mirror; focusing diffracted light from a pattern not including defection onto a photosensitive plate by a lens, while moving the mirror so that the incident angle of coherent light to the pattern not including defection on a model specimen varies within a predetermined range; and developing the exposed photosensitive plate.

A method of manufacturing a spatial frequency filter used in a pattern defect detection device according to yet another aspect of the present invention includes the steps of: directing coherent light to a pattern not including defection on a model specimen; focusing diffracted light from the pattern not including defection onto a photosensitive plate by a lens; exposing the photosensitive plate with diffracted light while moving the photosensitive plate within a predetermined range in two dimensional directions crossing diffracted light; and developing the exposed photosensitive plate.

A method of manufacturing a spatial frequency filter used in a pattern defect detection device according to yet a further aspect of the present invention includes the steps of: directing coherent light to a pattern not including defection on a model specimen; exposing a plurality of layered photosensitive plates by diffracted light from the pattern not including defection; and developing the exposed multilayered photosensitive plates.

A method of manufacturing a spatial frequency filter used in a pattern defect detection device according to yet a still further aspect of the present invention includes the steps of: directing coherent light to a pattern not including defection on a model specimen; exposing a first photosensitive plate by diffracted light from the pattern not including defection; developing the exposed first photosensitive plate; exposing by diffracted light a second photosensitive plate superimposed behind the exposed first photosensitive plate; and developing the exposed second photosensitive plate, to obtain a spatial frequency filter including developed first and second photosensitive plates.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS

Figure 3:
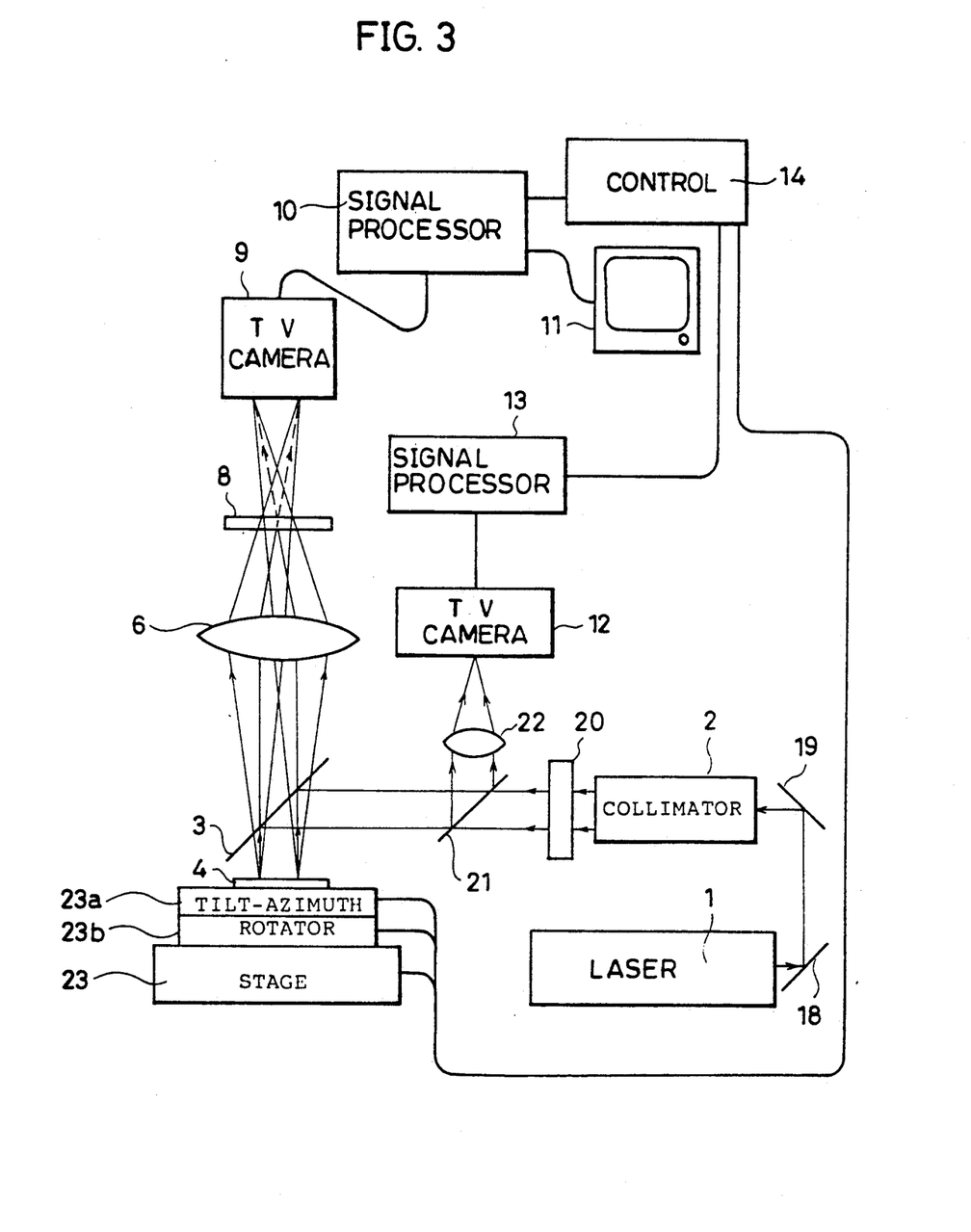
FIG. 3 is a block diagram depicting an embodiment of the present invention.

Referring to FIG. 3, a first embodiment of the present invention is schematically shown in a block diagram. The pattern defect detection device of FIG. 3 comprises reflecting mirrors 18 and 19, a shutter mechanism 20 for controlling the transmittance of parallel ray from a collimator 2, a half mirror 21, a lens 22 for focusing the parallel ray reflected by half mirror 21, and a stage 23 on which a specimen 4 is placed for changing the tilt of specimen 4 to emit a detection signal (diffracted light) having a different diffraction angle to a spatial frequency filter 8. Stage 23 comprises a tilt-azimuth angle adjustment mechanism 23a and a rotation mechanism 23b around a vertical axis. Since the components in FIG. 3 having reference numbers identical to those of FIG. 1 indicate the same components, their descriptions will not be repeated.

The operation of the device of FIG. 3 will be explained hereinafter. A spatial frequency filter 8 is fabricated before initiating detection of defection on specimen 4 such as a semiconductor integrated circuit wafer. In the fabrication of spatial frequency filter 8, the intensity of diffracted light is detected from a pattern not including defection on a model specimen 4 at the back focal plane of lens 9 where photosensitive plate 8 is placed to determine the exposure time for fabricating the filter. Assuming that the standard exposure energy of the filter photosensitive material is 100 mJ/cm$^2$, and the arrival average luminous energy at the back focal plane of lens 6 is 10 mW, the optimum exposure time is:

$$100 \text{ (mJ/cm}^2\text{)} \div 10\text{(mW)} = 10 \text{ (sec.)}$$

Photosensitive plate 8 may be exposed continuously for 10 seconds, or a total of ten seconds for several exposures may be carried out. During this exposure, stage 23 is operated by an instruction from controller 14, whereby the tilt-azimuth angle is changed so that the angle of reflection on the surface of model specimen 4 changes within a predetermined range.

Figure 4A:
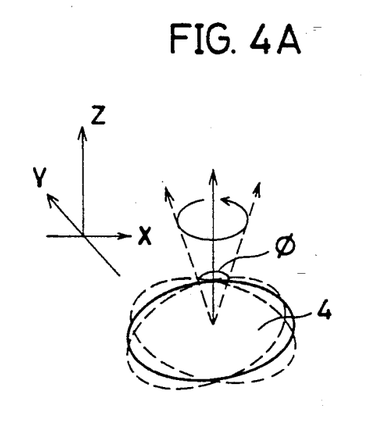
FIGS. 4A, 4B and 4C are diagrams for explaining the operation of the device of FIG. 3.
Figure 4B:
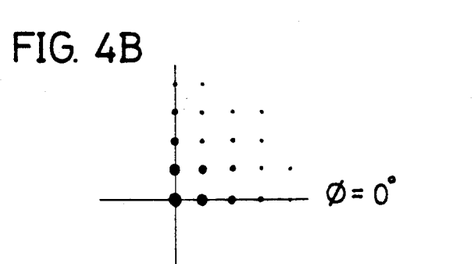
Figure 4C:
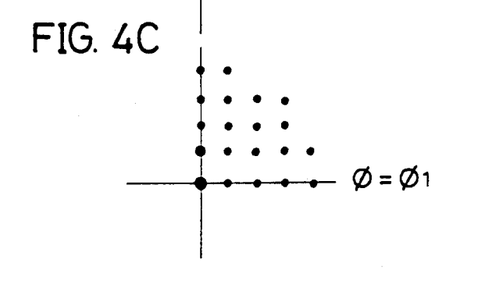

Referring to FIG. 4A, the variation of the tilt-azimuth angle of specimen 4 is depicted. The X axis and the Y axis represent horizontal planes, and the Z axis represents the vertical axis. The tilt angle $\phi 0$ of the normal line of the surface of specimen 4 to the Z axis is set to a predetermined value, and the azimuth angle is varied from 0° to 360°. FIG. 4B shows a portion of the black spot pattern on spatial frequency filter 8 formed when tilt angle $\phi = 0°$. FIG. 4C shows a portion of the black spot pattern on spatial frequency filter 8 formed by changing the azimuth angle when tilt angle $\phi = \phi_1$. In the case where the tilt-azimuth angle is not changed and tilt angle $\phi = 0°$, the diameter of the black spot on filter 8 becomes smaller in proportion to that of a diffracted spot of a higher order. In the case where the tilt-azimuth angle is varied within a predetermined range, the diameter of the black spot on the created filter 8 has a tendency to be increased in proportion to that of a diffracted spot of a higher order.

The value of tilt angle $\phi$ which increases the black spot diameter is often provided as an empirical value. Tilt angle $\phi$ is set to a value approximately 10% larger than the value of the wave on the surface of a thermal treated semiconductor integrated circuit wafer serving as specimen 4. The value of this undulating surface is represented as a tilt angle obtained by conversion calculation. Satisfactory recording of diffracted light of higher order can be obtained by an exposure time which is 2 to 3 times longer than the optimum exposure time i.e. by increasing the standard exposure energy by 2 to 3 times. Because this depends upon the fourier transform pattern appearing at the back focal plane, the exposure time is determined empirically for each pattern.

There are two methods for this exposure. According to the first method, the azimuth angle of the tilting direction is varied slowly from 0° to 360° around the optical axis with a constant tilt angle $\phi$ of specimen 4, while light energy is directed to photosensitive plate 8 for a certain exposure time (for example, 10 seconds in the first embodiment). Diffracted information in every azimuth direction to tilt angle $\phi$ will be recorded on photosensitive plate 8. According to the second method, a multi-exposure of n times is carried out. The tilt angle $\phi$ is set to a constant value with the rotation angle in the X - Y plane equally divided into n, whereby the exposure time period is also divided into n. This multi-exposure exposure has an advantage that the transmittance efficiency of a detection signal by spatial frequency filter 8 is not so reduced for specimens having few diffracted light of higher order.

Although a spot corresponding to diffracted light of lower order with high light intensity has a greater increase in diameter when filter 8 is formed under a long exposure time period without changing the tilt-azimuth angle, a spot corresponding to diffracted light of higher order in the first embodiment where diffracted light is recorded while changing the tilt-azimuth angle has a greater transfer distance on photosensitive plate 8 by the azimuth rotation. That is to say, the spot diameter has a greater increasing rate in proportion to a spot corresponding to diffracted light of higher order, as mentioned above in association with FIGS. 4B and 4C.

Thus, a spatial frequency filter 8 is obtained by developing the above-described exposed photosensitive plate 8. This filter 8 is positioned and secured again at the back focal plane of lens 6.

A specimen 4 which may have some defection is inspected by a pattern defect detection device of FIG. 3 using the above-described spatial frequency filter 8. Light emitted from laser oscillator 1 is reflected by half mirror 3 to be directed to specimen 4 such as a semiconductor integrated circuit wafer. The portion of diffracted light from specimen 4 passing half mirror 3 is converged by lens 6 to be focused. Spatial frequency filter 8 is positioned at the back focal plane of lens 6 to remove diffracted light of a proper pattern.

Since the diffracted pattern on spatial frequency filter 8 is recorded by varying the diffraction angle of the surface of model specimen 4 having a pattern not including defection, diffracted light of proper pattern can be reliably removed even if there is a wave on the surface of specimen 4 generated by thermal treatment. Therefore, only the defection signal light is sent to detection signal light detection camera 9 portioned at the focusing plane of lens 6, whereby the defection is displayed on monitor 11 by signal processing of first signal processor 10.

Even if the surface of specimen 4 is undulating, pattern defect detection can be rapidly carried out without the need of accurate registration of the diffracted pattern of spatial frequency filter 8 and the diffracted light from specimen 4.

Figure 5:
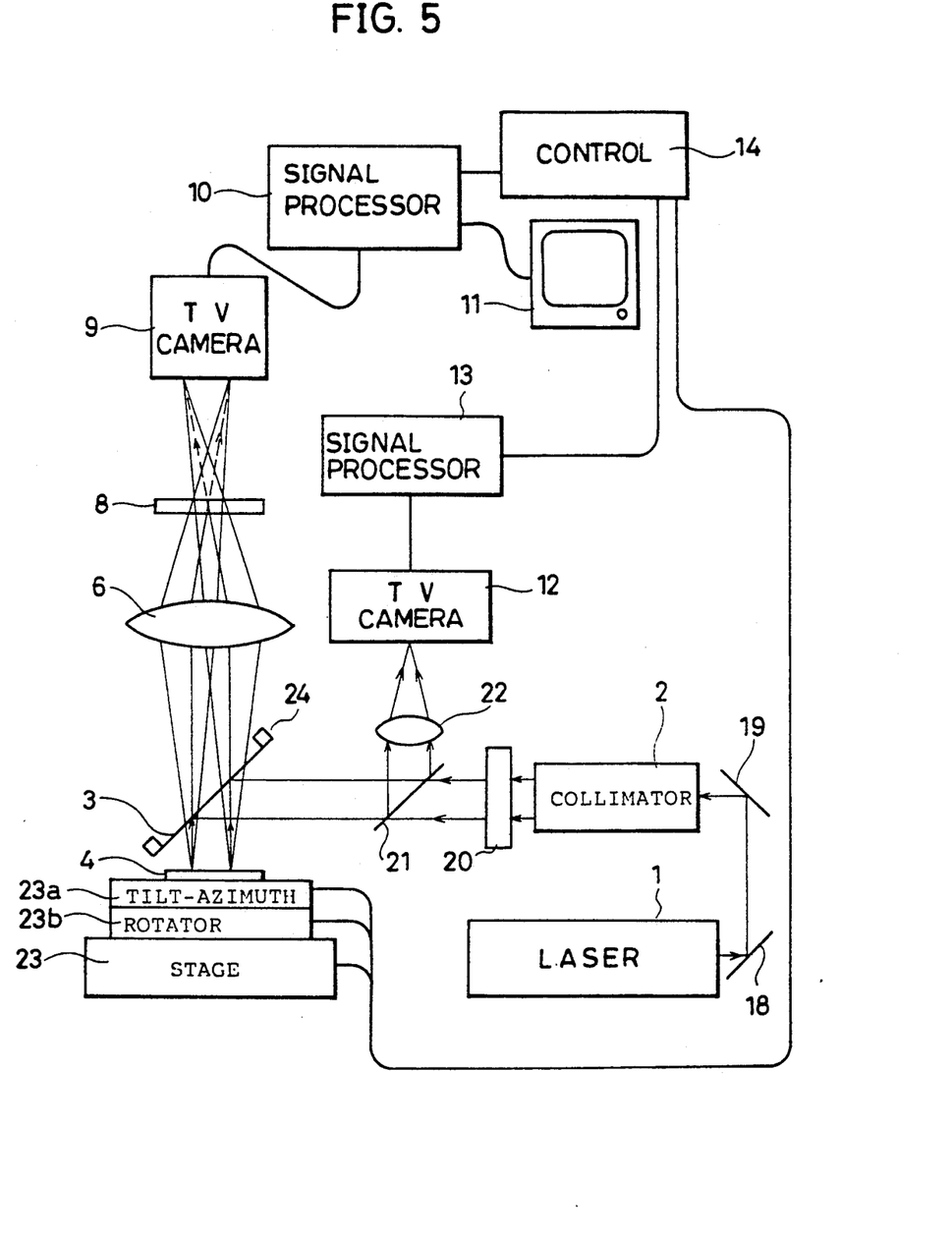
FIG. 5 is a block diagram depicting a second embodiment.
Figure 6:
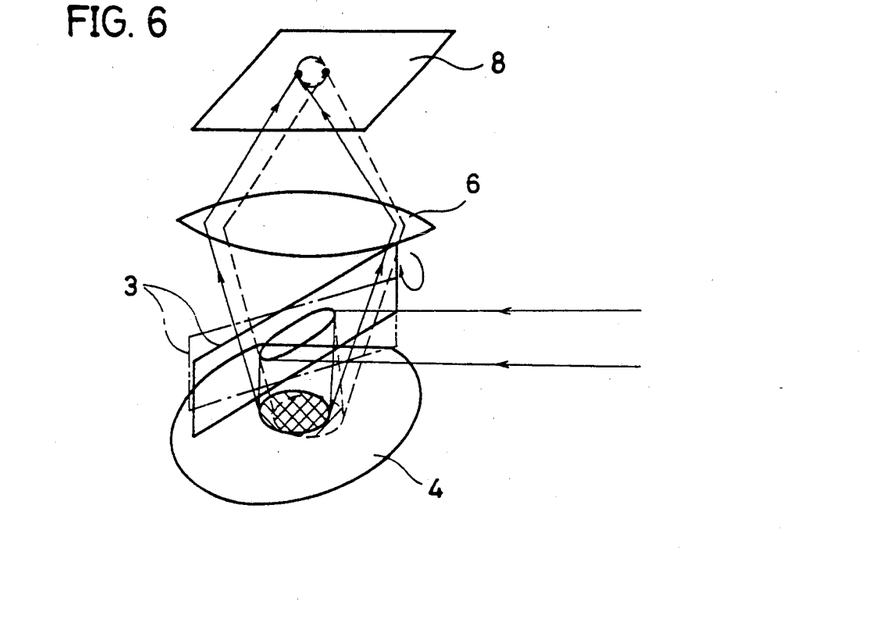
FIG. 6 is a perspective diagram for explaining the operation of the device of FIG. 3.

Referring to FIG. 5, a second embodiment of the present invention is shown. The device of FIG. 3 is similar to that of the FIG. 3, with a mirror angle moving mechanism 24 added that can change the reflected angle of reflection of half mirror 3 within a predetermined range. In the second embodiment, mirror angle moving mechanism 24 is controlled by an instruction from controller 14 to operate half mirror 3 during the time period diffracted light is directed to photosensitive plate 8. It is appreciated from the enlarged perspective view of FIG. 6 that the tilt angle $\phi$ of specimen 4 is made constant, and the azimuth angle of the tilting direction is varied slowly from 0° to 360° around the optical axis. Alternatively, the azimuth angle is rotated during the entire time period of exposure at short cycles. Therefore, information of diffracted light by various incident angles is recorded on photosensitive plate 8 without changing the tilt-azimuth angle of stage 23.

Since the operation of detecting specimen 4 which may have some defection with the pattern defect detection device of FIG. 3 using spatial frequency filter 8 obtained by the second embodiment is similar to the operation of the first embodiment, the description thereof will not be repeated.

Figure 7:
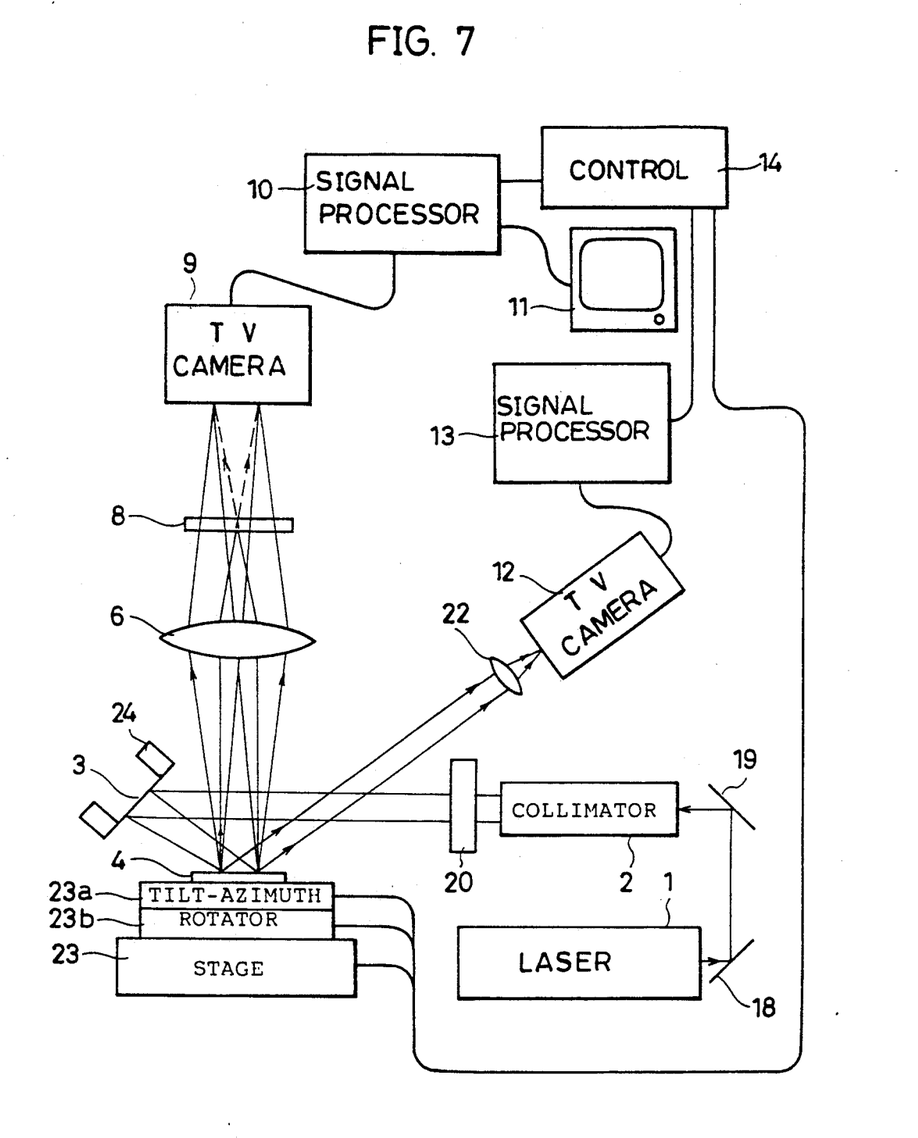
FIG. 7 is a block diagram depicting a third embodiment.
Figure 8:
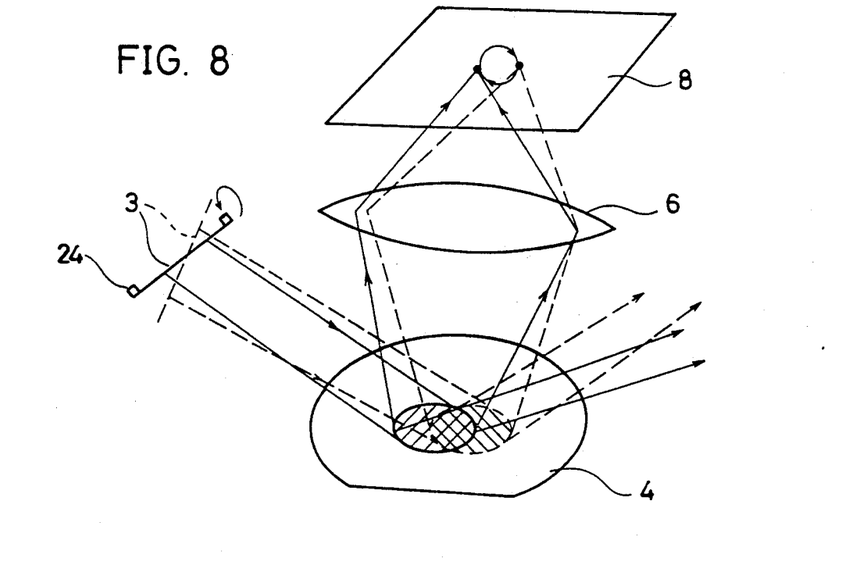
FIG. 8 is a perspective view showing the operation of the device of the FIG. 7.

Referring to FIG. 7, a third embodiment of the present invention is depicted. The device of FIG. 7 is similar to that of FIG. 5, except that a mirror 3a directs coherent light onto the surface of the specimen from an oblique direction. Therefore, not a half mirror, but a complete reflection mirror is used as mirror 3a. The manner of exposing an photosensitive plate in the third embodiment is similar to that of the second embodiment, as depicted in the enlarged perspective diagram of FIG. 8.

Figure 9:
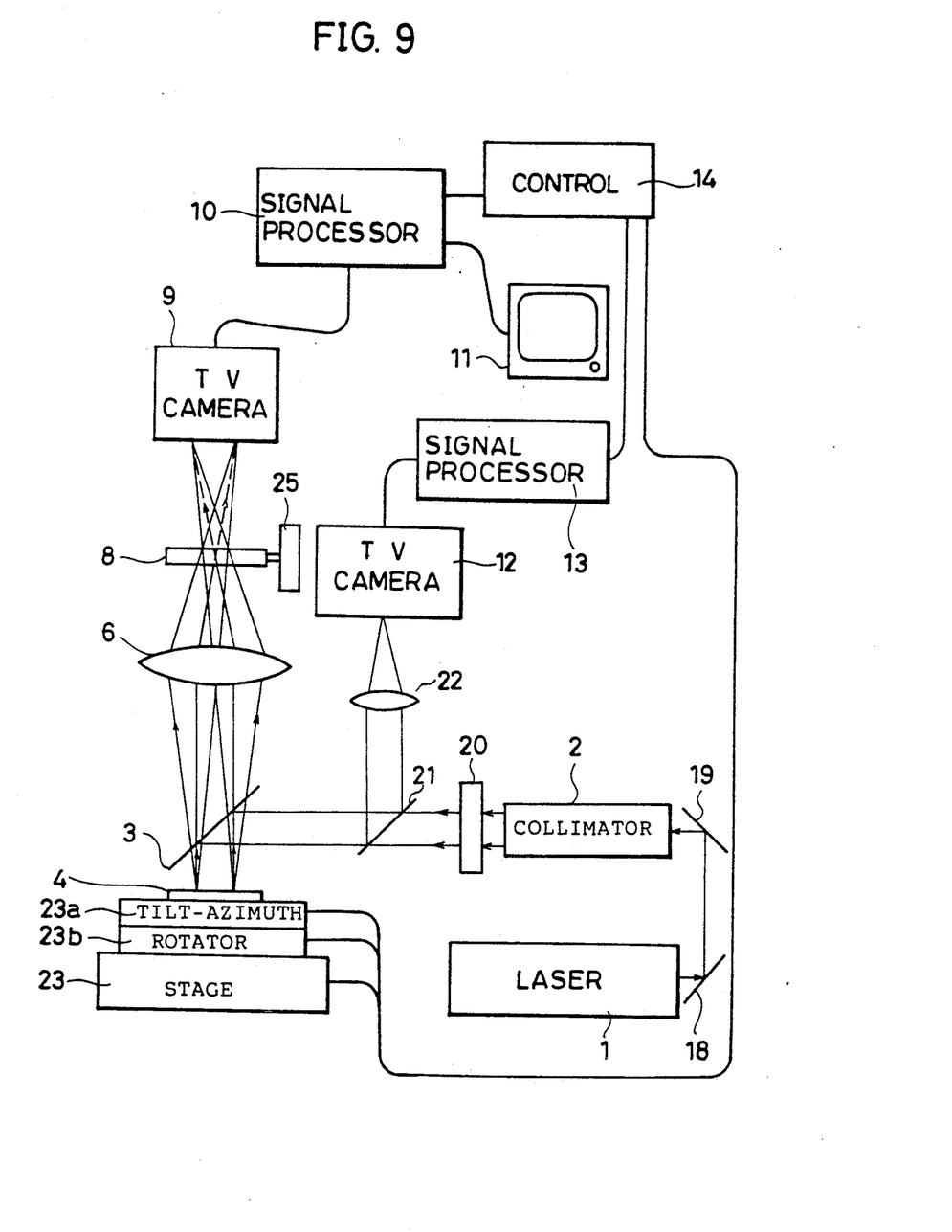
FIGS. 9, 10 and 11 are block diagrams showing the fourth, fifth, and sixth embodiments.

Referring to FIG. 9, a fourth embodiment of the present invention is depicted. The device of FIG. 9 is similar to that of FIG. 3, except that a plate moving mechanism 25 is added that can move photosensitive plate 8 within a predetermined range in two dimensional directions traversing diffracted light. In the fourth embodiment, photosensitive plate 8 is minutely moved by plate moving mechanism 25 in two dimensional directions traversing diffracted light to depict a predetermined small circle while photosensitive plate 8 is exposed to diffracted light. As a result, the size of the diffracted spot recorded on photosensitive plate 8 is expanded by a controlled amount, as in the case of the first embodiment.

Figure 10:
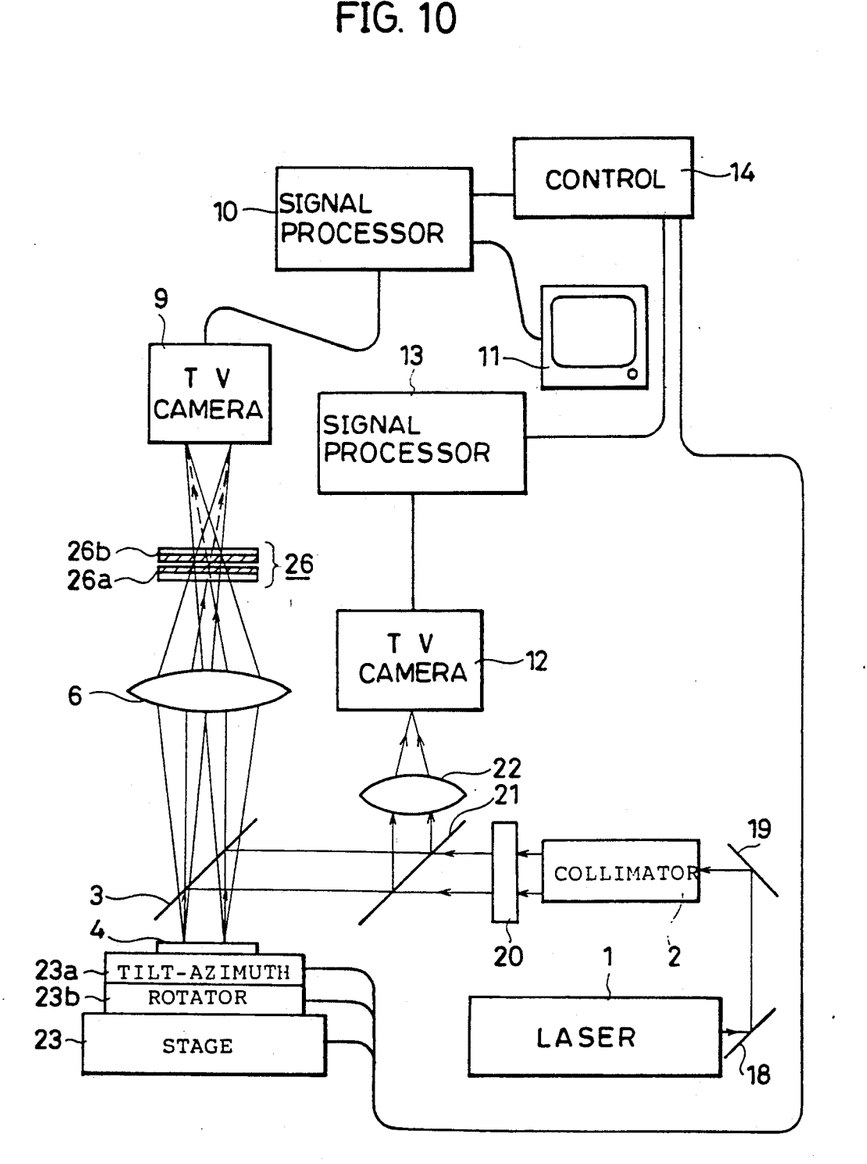

Referring to FIG. 10, a fifth embodiment of the present invention is depicted. The device of FIG. 10 is similar to that of FIG. 3, except that spatial frequency filter 26 is formed by a plurality of layers of photosensitive plates. In the embodiment of FIG. 10, spatial frequency filter 26 comprises first and second photosensitive plates 26a and 26b layered upon each other. Each of photosensitive plates 26a and 26b include an emulsion layer represented by a hatched layer in the drawing.

The two photosensitive plates 26a and 26b are exposed simultaneously by diffracted light from model specimen 4 having a pattern not including defection. This means that photosensitive plates 26a and 26b have the same diffraction pattern recorded. By passing diffracted light through the above-described spatial frequency filter 26, an effect substantially equal to that where diffracted light is passed two times through a filter 8 formed by one photosensitive plate can be obtained. Spatial frequency filter 26 can block diffracted light from the proper pattern on specimen 4 in a more reliable manner to decrease sufficiently a background noise signal. Therefore, detection of a weak defection signal light is possible. In other words, spatial frequency filter 26 allows detection of higher sensitivity by the pattern defect detection device of FIG. 10.

Although two photosensitive plates 26a and 26b are shown in the embodiment of FIG. 10, they may be substituted by one photosensitive plate where an emulsion layer is applied on both sides of one base plate.

Figure 11:
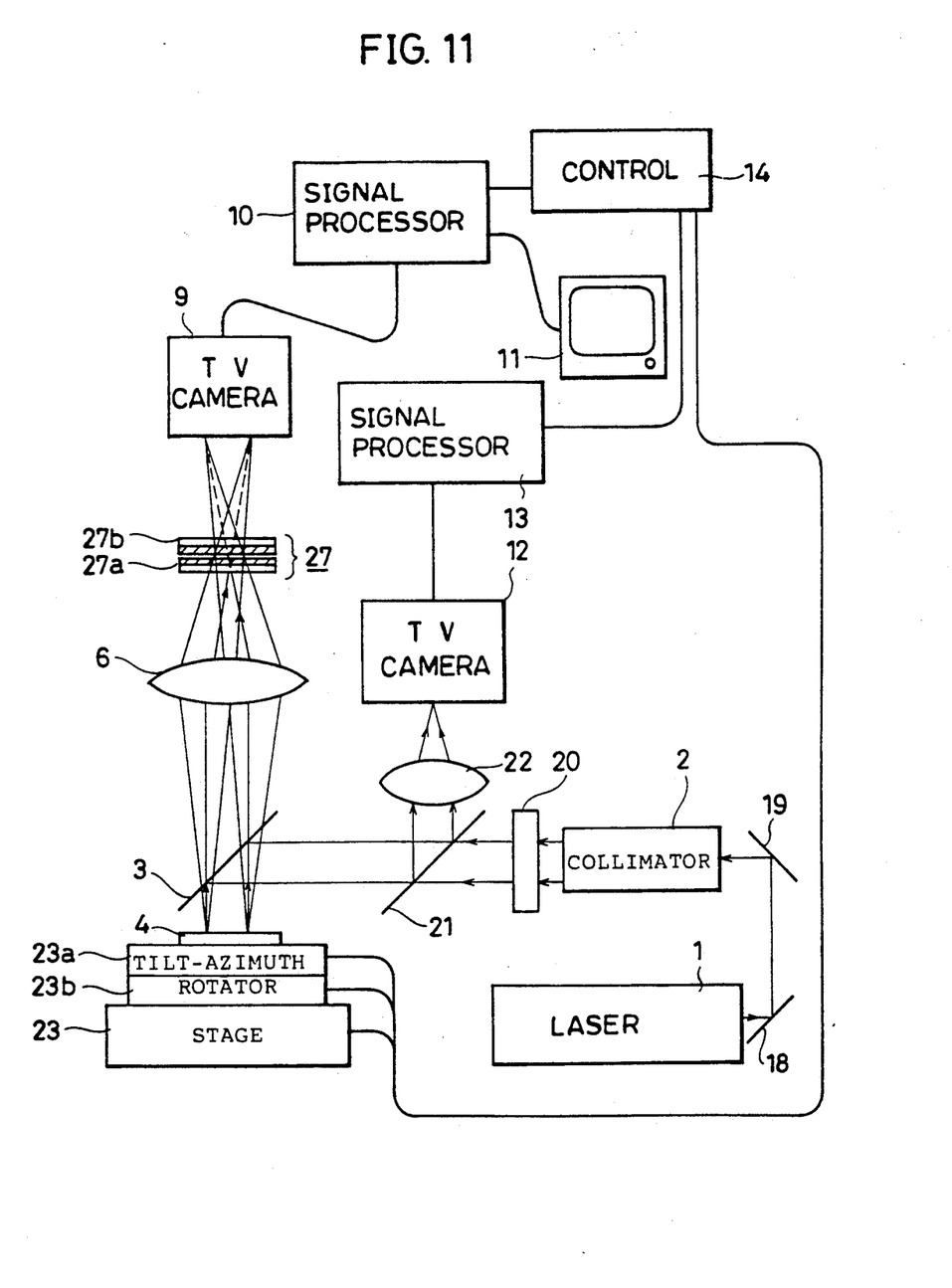

Referring to FIG. 11, a sixth embodiment of the present invention is depicted. The sixth embodiment is similar to the fifth embodiment, except that spatial frequency filter 27 is created as below using first and second photosensitive plates 27a and 27b.

First, only the first photosensitive plate 27a is placed at the back focal plate of the lens 6. This plate is exposed by diffracted light from model specimen 4 having a pattern, and then developed. If model specimen 4 includes a first pattern of a high repetition number and a second pattern of a low repetition number, first photosensitive plate 27a is exposed under the condition of recording in an optimum manner the Fourier transform pattern (diffraction pattern) of high light intensity from the first pattern.

Then, the developed first photosensitive plate 27a is placed again at the back focal plane of lens 6, with a second photosensitive plate 27b superimposed behind first photosensitive plate 27b. Since diffracted light from the first pattern of the high repetition number on model specimen 4 is blocked by the developed first photosensitive plate 27a, the second photosensitive plate 27b is exposed under the condition of recording in an optimum manner the fourier transform pattern of low light intensity from the second pattern of the low repetition number. This means that the weak diffracted light from the second pattern which was not sufficiently recorded on the first photosensitive plate 27a at the time of its exposure due to its low light intensity will be recorded on the second photosensitive plate 27b at the time of exposure of second photosensitive plate 27b.

Therefore, diffracted light from a proper pattern is reliably blocked so that only defection signal light is extracted at high sensitivity to be received by defect detection camera 9, even in the case where a pattern of many repetitive components and a pattern of few repetitive components exist on specimen 4 by using the above described spatial frequency filter 27.

Figure 12A:
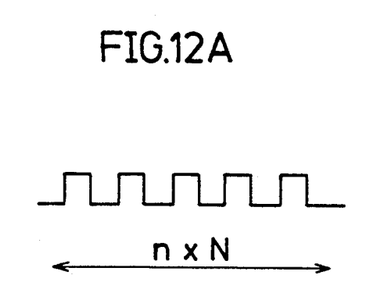
FIGS. 12A, 12B, 12C and 12D are diagrams showing the relationship between repetitive pattern and Fourier transform pattern.
Figure 12B:
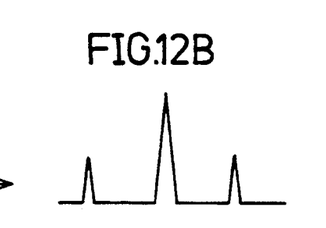
Figure 12C:
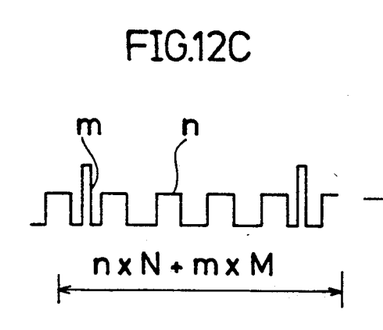
Figure 12D:
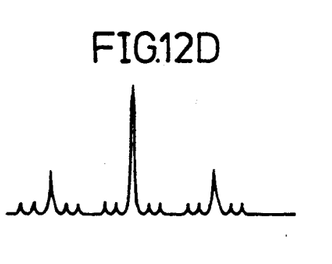

Referring to FIG. 12A-12D, the relation between the repetitive pattern and the Fourier transform pattern is shown. FIG. 12A shows one dimension pattern having a repetition pitch n and a repetition number N. FIG. 12B schematically shows the one-dimensional Fourier transform intensity profile of FIG. 12A, in which the horizontal direction represents the position, and the vertical direction represents the intensity of the diffracted light. FIG. 12C shows a mixture of patterns including a first pattern having a repetition pitch n and repetition number N, and a second pattern having a repetition pitch m and a repetition number M. FIG. 12D schematically shows the one-dimensional Fourier transform intensity profile of the synthesized pattern including the first and second patterns of FIG. 12C. It can be appreciated from FIG. 12D that diffracted light intensity is low from the pattern of the low repetition number, with a broad intensity distribution.

The defection signal from defect detection camera 9 is processed in first signal processor 10, whereby an image of defection is displayed on TV monitor 11. At this time, the amount of change of the reflection angle of specimen 4 detected by position detection camera 12 is converted to an offset distance of the Fourier transform pattern via second signal processor 13. Controller 14 provides a correction instruction regarding the tilt-azimuth angle of stage 23 according to this converted value.

Although a Fourier transform pattern of the pattern having a high repetition number is recorded on one photosensitive plate 27a in the embodiment of FIG. 11, it is appreciated that a Fourier transform pattern of a high repetition number pattern may be recorded simultaneously onto two photosensitive plates, followed by recording the Fourier transform pattern of a low repetition number pattern on a third photosensitive plate.

However, it should be noted that the spatial frequency filter should not include too many component plates since the intensity of the defection signal light is slightly attenuated every time it passes each component plate of the spatial frequency filter. Furthermore, a spatial frequency filter including too many component plates will result in increase of thickness. This is not desirable because the offset distance between the component plates and the back focal plane of lens 6 will become greater.

Although the above embodiments were described in which defection detection was carried out for a semiconductor integrated circuit wafer, the present invention may be applied to the defect detection of other specimens having repetitive patterns such as a TFT liquid crystal display.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. A pattern defect detection device comprising:
   a stage for supporting a specimen having a repetitive pattern on the surface thereof;
   a light source for emitting coherent light,
   mirror means for directing said light to the pattern on said specimen, said mirror means including mirror angle changing means for changing the angle of reflection of said light,
   a lens for focusing light diffracted by the pattern on said specimen,
   plate holding means for holding at the back focal plane of said lens either of at least one photosensitive plate to form a spatial frequency filter, and a created spatial frequency filter including at least one plate having a pattern, and
   detection signal detect means for detecting light transmitting said spatial frequency filter as a detection signal corresponding to defection in the pattern of said specimen.

2. A pattern defect detection device in accordance with claim 1, the angle of said mirror can be changed within one degree.

3. A pattern defect detection device in accordance with claim 1, said mirror angle changing means has two tilting axes which are not parallel to each other.

4. A pattern defect detection device in accordance with claim 1, wherein said plate holding means holds either of a plurality of said photosensitive plates and said created spatial frequency filter including a plurality of said plate.

5. A pattern defect detection device in accordance with claim 2, where said plate holding means holds either of a plurality of said photosensitive plates and said created spatial frequency filter including a plurality of said plate.

6. A spatial frequency filter in accordance with claim 3, comprising a plurality of said plate.

7. A pattern defect detection device comprising:
   a stage for supporting a specimen having a repetitive pattern on the surface thereof,
   a light source for emitting coherent light,
   mirror means for directing said light to the pattern on said specimen,
   a lens for focusing light diffracted by the pattern on said specimen,
   plate holding means for holding at the back focal plane of said lens either of at least one photosensitive plate to form a spatial frequency filter, and a created spatial frequency filter including at least one plate having a pattern, said plate holding means including moving means for moving either of at least one said photosensitive plate and said created spatial frequency filter in two dimensional directions traversing said diffracted light, and detection signal detect means for detecting light transmitted through said spatial frequency filter as a detection signal corresponding to detection in the pattern of said specimen.

8. A spatial frequency filter used in a pattern defect detection device, comprising a pattern which comprises black spots, each having a diameter expanded by a controlled amount in comparison with a corresponding black spot diameter on a photosensitive plate obtained by exposure by diffracted light from a model spectrum which contains no defects.

* * * * *